US00PP37110P3

(12) United States Plant Patent
Huber

(10) Patent No.: US PP37,110 P3
(45) Date of Patent: Nov. 25, 2025

(54) ***DAHLIA* PLANT NAMED 'LeeAnn's FD47C'**

(50) Latin Name: *Dahlia hybrida*
Varietal Denomination: LeeAnn's FD47C

(71) Applicant: Coseytown Flowers llc, State Line, PA (US)

(72) Inventor: LeeAnn Huber, Greencastle, PA (US)

(73) Assignee: Coseytown Flowers LLC, State Line, PA (US)

( * ) Notice: Subject to any disclaimer, the term of this patent is extended or adjusted under 35 U.S.C. 154(b) by 0 days.

(21) Appl. No.: 18/999,407

(22) Filed: Dec. 23, 2024

(65) Prior Publication Data

US 2025/0261570 P1 Aug. 14, 2025

Related U.S. Application Data

(60) Provisional application No. 63/552,441, filed on Feb. 12, 2024.

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
See application file for complete search history.

*Primary Examiner* — Shubo Zhou
*Assistant Examiner* — Zachariah Allan Kay

(57) ABSTRACT

A new and distinct cultivar of *Dahlia* plant named 'LeeAnn's FD47C' is disclosed, characterized by a strong, upright growth habit, combined with free and early flowering. Flowers are held above the foliage canopy and have a consistent quality throughout the growing season. Flowering stems have an above average strength with a firm blossom attachment. Flower color is a unique shade of yellowish-pink which is new to the market. Inflorescences have strong postproduction quality. The new variety is a *Dahlia* typically produced for cut flower purposes, or garden or landscape.

2 Drawing Sheets

Figure 1:
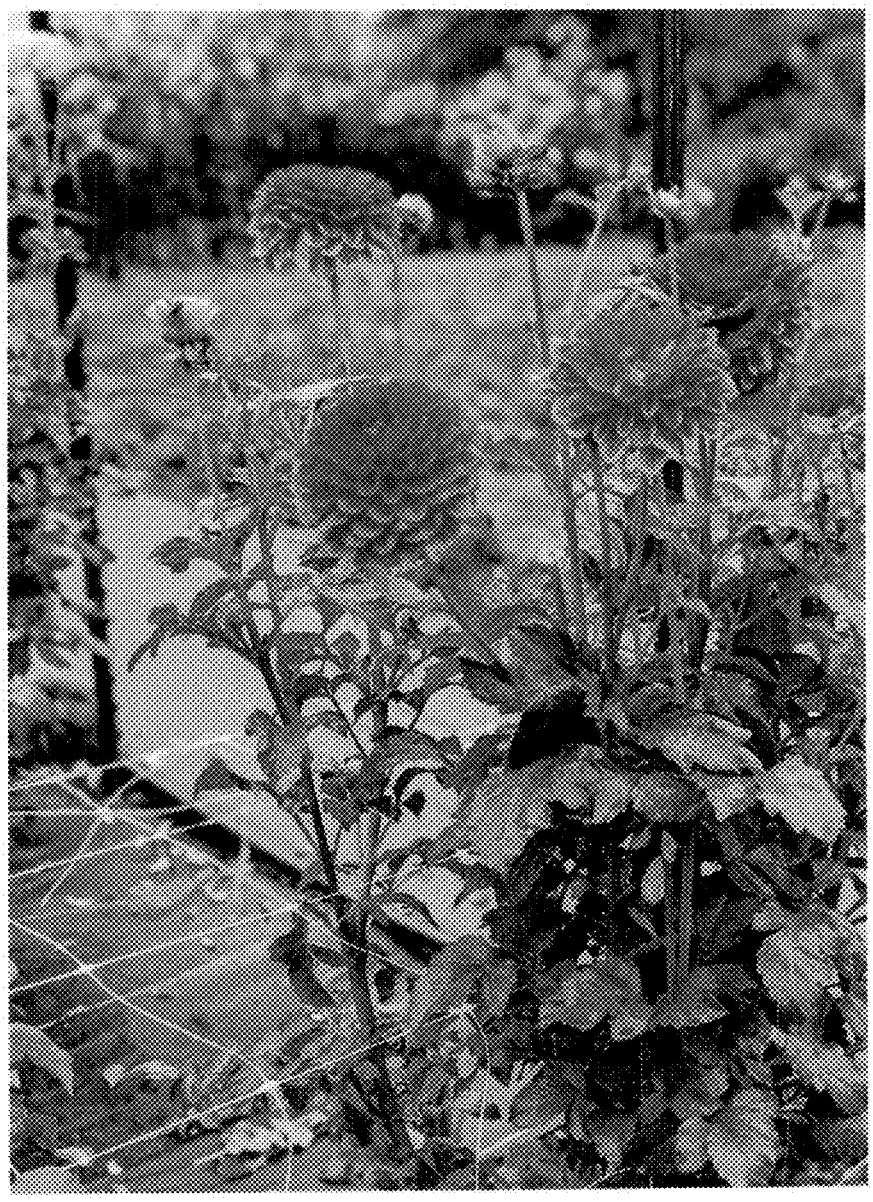

Latin name of the genus and species: *Dahlia hybrida.*
Variety denomination: 'LeeAnn's FD47C'.

BACKGROUND OF THE INVENTION

The new *Dahlia* cultivar is a product of a planned breeding program conducted by the inventor, in Greencastle, Pennsylvania. The objective of the breeding program was to produce new *Dahlia* varieties with improved performance in open field conditions and produce cut flowers suitable for transport and sale. The open-pollination resulting in this new variety was made during 2018.

The seed parent is the unpatented, variety of *Dahlia* 'Snoho Sonia'. The pollen parent is unidentified. Seed from 'Snoho Sonia' was collected in 2018 and grown in a cultivated garden area in 2019. 'LeeAnn's FD47C' was intentionally selected from the seedlings that resulted based on the criteria of stem length and strength, upright growth habit, blossom attachment, petal count, and bloom color.

Asexual reproduction of the new cultivar was first performed by tubers by the inventor in Greencastle, Pennsylvania in the Spring of 2020 and has shown that the unique features of this cultivar are stable and reproduced true to type in successive generations.

SUMMARY OF THE INVENTION

The cultivar 'LeeAnn's FD47C' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LeeAnn's FD47C' These characteristics in combination distinguish 'LeeAnn's FD47C' as a new and distinct *Dahlia* cultivar:

1. Strong, upright growth habit.
2. Free branching.
3. Early flowering.
4. Consistency of bloom quality throughout the growing season.
5. Flower held above the leaf canopy.
6. Above average stem strength. Stem strength is measured by assessing if any flexion occurs on harvested flower stems of 35 to 40 cm when the stem is given a brief, firm shake. Any stems which flex are considered average, stems which show damage are below average and stems which remain inflexible are above average.
7. Firm blossom attachment.
8. Unique deep yellowish/pink flower color, new to the US cut flower market.
9. Strong postproduction inflorescence quality.

Plants of the new cultivar 'LeeAnn's FD47C' are similar to plants of the seed parent, in some horticultural characteristics, however, plants of the new cultivar 'LeeAnn's FD47C' differ in the following;

1. The new variety has a larger, much darker flower compared to the ball form, lavender flower of the seed parent.

The pollen parent cannot be identified with certainty.

COMMERCIAL COMPARISONS

Plants of the new cultivar 'LeeAnn's FD47C' are comparable to the variety *Dahlia* 'Cornel', unpatented. The two

*Dahlia* varieties are similar in most horticultural characteristics; however, the new variety 'LeeAnn's FD47C' differs in the following:

1. Flowers of the new variety are a decorative form; flowers of this comparator are ball form.
2. Flower color of the new variety is a different shade of red than 'Cornel'.
3. Plants of the new variety are shorter than plants of 'Cornel'.
4. Plants of the new variety are more free flowering than plants of 'Cornel'.

BRIEF DESCRIPTION OF THE PHOTOGRAPHS

The accompanying photograph in FIG. 1 illustrates in full color a typical flowering plant of 'LeeAnn's FD47C' grown outdoors, in the ground under cut flower production conditions. Age of the plant photographed is approximately 18 weeks from a tuber.

Figure 2:
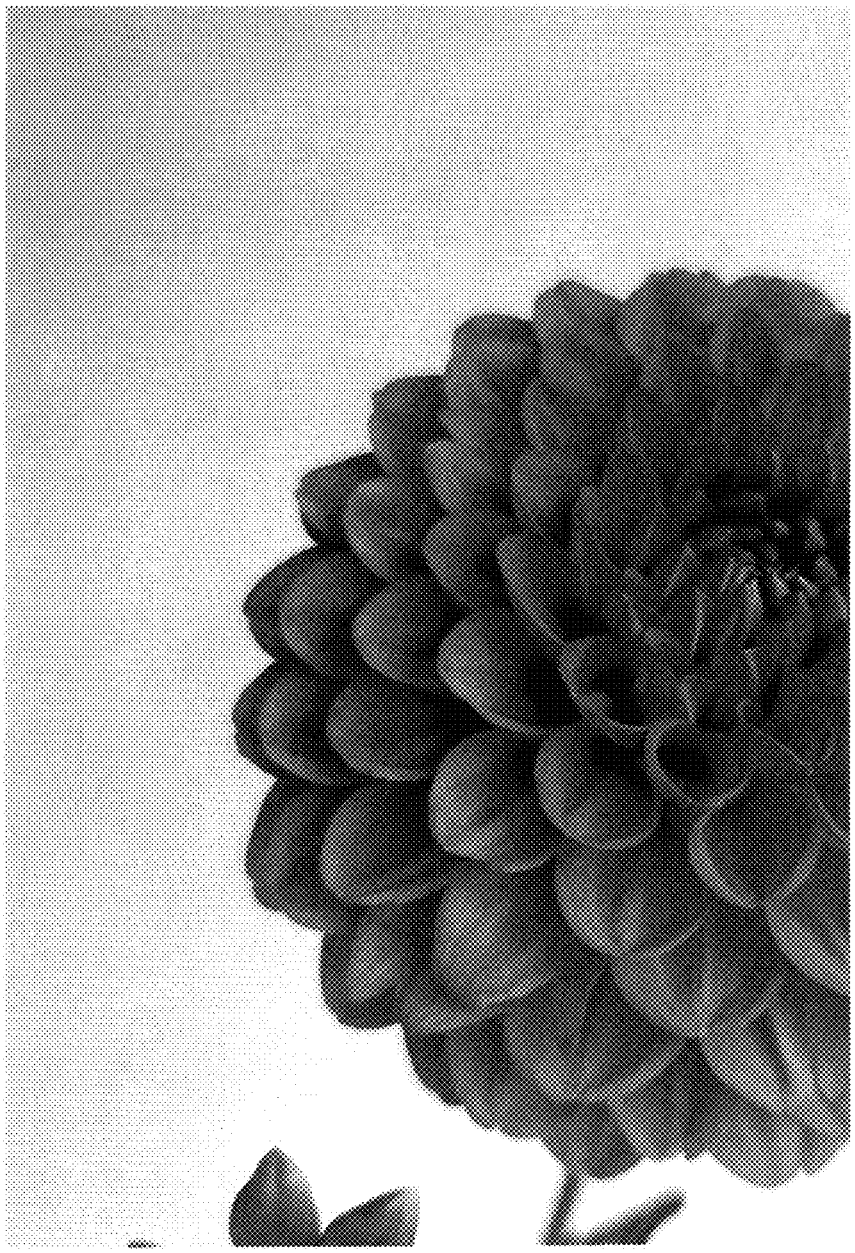

FIG. 2 illustrates a close-up of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society R.H.S. Colour Chart 2015 except where general terms of ordinary dictionary significance are used. The following observations and measurements describe 'LeeAnn's FD47C' plants grown outdoors, in Greencastle, PA. Age of the plants is approximately 6 months from a mature tuber. The growing temperature ranged from about 5° C. to 30° C. during the day and from 3° C. to 10° C. during the night. General light conditions are bright, normal sunlight. Measurements and numerical values represent averages of typical plant types.

Botanical classification: *Dahlia hybrida* 'LeeAnn's FD47C'.

PROPAGATION

Type of propagation typically used: Vegetative terminal cuttings or tubers.

PLANT

Plant type: Herbaceous flowering perennial.

Growth habit: Upright and freely branching with flowers held above foliage. Vigorous growth and regrowth after continuous harvesting of flowers.

Height: 127 cm.

Plant spread: 42.5 cm.

Growth rate: Vigorous, blooming begins 65 days after field planting and extends until frost, maintaining renewed lateral branch growth and bud formation into the shorter daylight hours of Autumn.

Branching characteristics: Free-branching, lateral branches on average 48 cm long.

FOLIAGE

Leaf:

*Shape*.—Ovate.

*Apex*.—Acute.

*Base*.—Oblique.

*Arrangement*.—Opposite. Single or composite with 3 to 5 leaflets.

*Length*.—Single leaves: About 79 mm. Compound leaves with three leaflets: About 101 mm. Compound leaves with five leaflets: About 125 mm.

*Width*.—Single leaves: about 48 mm. Compound leaves with three leaflets: about 103 mm. Compound leaves with five leaflets: about 107 mm.

*Attachment*.—Petiolate.

*Margin*.—Serrate.

*Texture of top surface*.—Glabrous.

*Texture of bottom surface*.—Glabrous.

*Color*.—Young foliage upper side: RHS Green 138A. Young foliage under side: RHS Green 138B. Mature foliage upper side: RHS Green 137C. Mature foliage under side: RHS Green 138B.

*Venation*.—Type: Palmate. Venation color upper side: Green 143C. Venation color under side: Green 143C.

Petiole:

*Single leaves*.—Length: 1. cm. Diameter: 2.5 mm.

*Compound leaves*.—Length: 4.5 cm. Diameter: 3 mm.

*Color*.—RHS Yellow-Green 144C with hints of Green 143A.

*Texture*.—Glabrous all surfaces.

FLOWER

Time to flower: Plants begin to bloom around 80 days after planting, continuously blooming until season ending frost.

Inflorescence and flower type and habit: Fully double decorative *Dahlia* flower. Upright blossom position.

Post production longevity: Inflorescences maintain good substance on the plant for about 14 days and for about 5 days as a cut flower.

Inflorescence size:

*Diameter*.—8.8 cm.

*Height*.—4.55 cm.

*Receptacle diameter*.—7 mm.

Bud:

*Shape*.—Oblate.

*Length*.—7.4 mm.

*Diameter*.—12 mm.

*Color*.—RHS Yellow-Green N144A.

*Texture*.—Glabrous.

Ray florets:

*Number of ray florets per inflorescence*.—About 160 arranged in 11 whorls.

*Length*.—About 35 mm.

*Width*.—About 19 mm.

*Shape*.—Obovate.

*Apex*.—Obtuse to rounded.

*Base*.—Attenuate.

*Aspect*.—Initially upright to slightly forward to the peduncle to cupped when completely reflexed.

*Texture*.—Upper surface — Smooth, velvety with gold diamond dust reflective qualities. Lower surface — Smooth, velvety with gold diamond dust reflective qualities.

*Color*.—Summer produced flowers: Upper surface immature: Red 47A. Lower surface immature: Red 47B. Upper surface mature: Red 47C. Lower surface mature: Red 47C. Autumn produced flowers: Upper surface immature: Red 47C. Lower surface immature: Red 47C. Upper surface mature: Red 42D. Lower surface mature: Red 42D.

Disc florets:

*Number of disc florets per inflorescence*.—About 65.

*Shape*.—Tubular.

*Apex*.—Acute.

*Length*.—About 7 mm.

*Diameter, base*.—About 1 mm.

*Color*.—Apex yellow 9C, midsection N25C, base 2B.

Phyllaries:

*Quantity per inflorescence*.—Average 9 arranged in a single whorl.

*Length*.—About 19 mm.

*Width*.—About 7.5 mm.

*Shape*.—Rhombic.

*Apex*.—Acute.

*Base*.—Truncate.

*Margin*.—Entire.

*Texture*.—Upper and lower surfaces smooth, glabrous, waxy.

Peduncle:

*Length*.—42 cm.

*Diameter*.—9 mm.

*Angle*.—Erect to about 14° from vertical.

*Strength*.—Exceptional with no bend or give.

*Texture*.—Glabrous, subtle sulcation.

*Color*.—RHS Yellow-Green 146C.

REPRODUCTIVE ORGANS

Disc florets:

Stamens:

*Number*.—5.

*Stamen attachment*.—Filament adnate to ventral surface of corolla

*Stamen length*.—About 9 mm.

Anthers:

*Length*.—About 4 mm.

*Width*.—Less than 1 mm.

*Shape*.—Linear.

*Pollen*.—Quantity: Moderate. Color: Yellow-Orange 17A.

Pistil:

*Number*.—1.

*Length*.—About 15.5 mm.

*Stigma shape*.—Bifurcate.

*Stigma length*.—About 2.5 mm.

*Stigma width*.—About 0.7 mm.

*Stigma color*.—Yellow-Orange 17B.

*Ovary*.—Position: Inferior. Shape: Truncate. Length: 2.5 mm. Width: 1.5 mm. Color: RHS Green-White 157A.

OTHER CHARACTERISTICS

Fruit/seed: About 12 mm long, 2.5 mm wide, colored near Brown 200A.

Disease/pest resistance: Neither resistance nor susceptibility to has been observed.

Weather and climate performance: Plants of the new *Dahlia* have excellent tolerance to heat and high UV index, resisting wilting and fading in field grown conditions. Daylight length has minimal effects on bud and bloom production, maintaining cut flower output into late season light and weather conditions.

What is claimed is:

1. A new and distinct cultivar of *Dahlia* plant named 'LeeAnn's FD47C' as herein illustrated and described.

* * * * *